(12) United States Patent
Benning et al.

(10) Patent No.: US 9,974,561 B2
(45) Date of Patent: May 22, 2018

(54) EUS GUIDED ACCESS DEVICE

(71) Applicant: Boston Scientific Scimed, Inc., Maple Grove, MN (US)

(72) Inventors: Christopher A. Benning, Hopkinton, MA (US); Andrew J. Whitney, Douglas, MA (US); Bryan Bannon, Duxbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 364 days.

(21) Appl. No.: 14/794,465

(22) Filed: Jul. 8, 2015

(65) Prior Publication Data

US 2016/0015421 A1    Jan. 21, 2016

Related U.S. Application Data

(60) Provisional application No. 62/024,747, filed on Jul. 15, 2014.

(51) Int. Cl.
*A61M 5/00* (2006.01)
*A61B 17/34* (2006.01)
(Continued)

(52) U.S. Cl.
CPC .... *A61B 17/3415* (2013.01); *A61B 17/00234* (2013.01); *A61B 17/3403* (2013.01);
(Continued)

(58) Field of Classification Search
CPC ............ A61B 17/3415; A61B 17/3478; A61B 17/3403; A61B 17/3417; A61B 17/3476; A61B 17/00234; A61B 18/1492; A61B 18/1477; A61B 2017/003311; A61B 2018/00867; A61B 2018/00535;
(Continued)

(56) References Cited

U.S. PATENT DOCUMENTS 2,256,942 A * 9/1941 Duffy ................. A61B 17/3415
                                                      137/614.12
5,403,311 A * 4/1995 Abele ................ A61B 18/1477
                                                      604/21
(Continued)

FOREIGN PATENT DOCUMENTS

JP      S9151969      8/1984
JP      2002527140    8/2002
(Continued)

*Primary Examiner* — Phillip R Wiest
(74) *Attorney, Agent, or Firm* — Fay Kaplun & Marcin, LLP

(57) ABSTRACT

A system for endoscopic ultrasound guided drainage includes an access sheath extending longitudinally from a proximal end to a distal end and including an access lumen extending therethrough from the proximal end to the distal end; a stylet slidably received within the access lumen, the stylet extending longitudinally from a proximal end to distal end and including a channel extending therethrough, the channel configured to receive a fluid therethrough; and a dilating sheath extending longitudinally from a proximal end to a distal end and including a dilating lumen extending therethrough. The dilating lumen is sized and shaped to slidably receive the access sheath.

21 Claims, 4 Drawing Sheets

(51) Int. Cl.
  *A61B 17/00* (2006.01)
  *A61B 18/14* (2006.01)
  *A61B 18/00* (2006.01)
  *A61M 27/00* (2006.01)
(52) U.S. Cl.
  CPC ...... *A61B 17/3417* (2013.01); *A61B 17/3476* (2013.01); *A61B 18/1492* (2013.01); *A61B 2017/00331* (2013.01); *A61B 2017/00867* (2013.01); *A61B 2017/3413* (2013.01); *A61B 2018/00535* (2013.01); *A61B 2018/00595* (2013.01); *A61B 2018/00982* (2013.01); *A61B 2218/007* (2013.01); *A61M 27/00* (2013.01); *A61M 2210/1071* (2013.01); *A61M 2210/1075* (2013.01)
(58) Field of Classification Search
  CPC ........... A61B 2018/00595; A61B 2018/00982; A61B 2018/007; A61M 27/00
  See application file for complete search history.

(56) References Cited

U.S. PATENT DOCUMENTS

| | | |
|---|---|---|
| 2005/0059890 A1 | 3/2005 | Deal et al. |
| 2006/0135963 A1 | 6/2006 | Kick et al. |
| 2007/0112302 A1 | 5/2007 | Yu |
| 2010/0081965 A1 | 4/2010 | Mugan et al. |
| 2010/0317963 A1 | 12/2010 | Clancy |
| 2013/0006145 A1 | 1/2013 | Toomey et al. |
| 2013/0090654 A1* | 4/2013 | Clancy ............... A61B 17/3478 606/45 |
| 2014/0005478 A1* | 1/2014 | Kennedy, II ........... A61B 1/012 600/114 |

FOREIGN PATENT DOCUMENTS

| | | |
|---|---|---|
| JP | 2013532557 | 8/2013 |
| WO | 2011/161474 | 12/2011 |

* cited by examiner

EUS GUIDED ACCESS DEVICE

PRIORITY CLAIM

The present application claims priority to U.S. Provisional Patent Application Ser. No. 62/024,747 filed Jul. 15, 2014; the disclosure of which is incorporated herewith by reference.

BACKGROUND

The pancreas and biliary system together form an important part of the digestive system. The pancreas and liver produce digestive fluids (pancreatic juice and bile) which help in the process of digestion (i.e., the breakdown of foods into parts which can be absorbed easily and used by the body). These digestive fluids are passed through the pancreatic duct and ducts of the biliary system prior to exiting into the intestine. Blockage of any of these ducts by, for example, a cancer, gallstone or scarring, may result in the duct becoming backed up and filled with fluid, requiring drainage.

SUMMARY

The present disclosure is directed to a system for endoscopic ultrasound guided drainage, comprising an access sheath extending longitudinally from a proximal end to a distal end and including an access lumen extending therethrough from the proximal end to the distal end, a stylet slidably received within the access lumen, the stylet extending longitudinally from a proximal end to distal end and including a channel extending therethrough, the channel configured to receive a fluid therethrough, and a dilating sheath extending longitudinally from a proximal end to a distal end and including a dilating lumen extending therethrough, the dilating lumen sized and shaped to slidably receive the access sheath.

In an embodiment, the access sheath may include a distal portion biased toward a curved configuration.

In an embodiment, the access sheath may be formed of a flexible polymeric material which permits the curved distal portion to be moved to a straightened configuration when the stylet is received therein.

In an embodiment, the curved configuration may be one of a pigtail loop, a J-shape and a shepherd's crook.

In an embodiment, the stylet may include a distal portion having a diameter larger than a remaining length of the stylet extending proximally from the distal portion.

In an embodiment, a portion of the channel extending through the distal portion of the stylet may be defined by an annular space extending about a longitudinal axis of the stylet.

In an embodiment, the system may further comprise a handle assembly coupled to a proximal end of each of the stylet, access sheath and dilating sheath.

In an embodiment, the handle assembly may include an actuator for moving the dilating sheath longitudinally relative to the access sheath.

In an embodiment, the dilating sheath may include an electrode at a distal end thereof configured to cauterize tissue.

In an embodiment, a distal portion of the stylet may have a larger diameter than a remaining portion of the stylet extending proximally therefrom, the diameter of the distal portion of the stylet corresponding to a diameter of the access lumen to facilitate puncturing of a target tissue.

In an embodiment, the system may further comprise a handle assembly coupled to a proximal end of each of the stylet, access sheath and dilating sheath.

In an embodiment, the handle assembly may include an actuator for moving the dilating sheath longitudinally relative to the access sheath.

The present disclosure is also directed to a method for endoscopic ultrasound guided drainage, comprising inserting an access sheath and a stylet through a working channel of an endoscope into a target duct within a body, the stylet extending through a lumen of the access sheath such that a distal tip of the stylet extends distally past a distal end of the access sheath so that the distal tip punctures the target duct, injecting a contrast media through a channel of the stylet into the target duct to visually verify that the target duct is filled with fluids, and advancing a dilating sheath distally over the access sheath and into the target duct to dilate the target duct.

DETAILED DESCRIPTION

Figure 1:
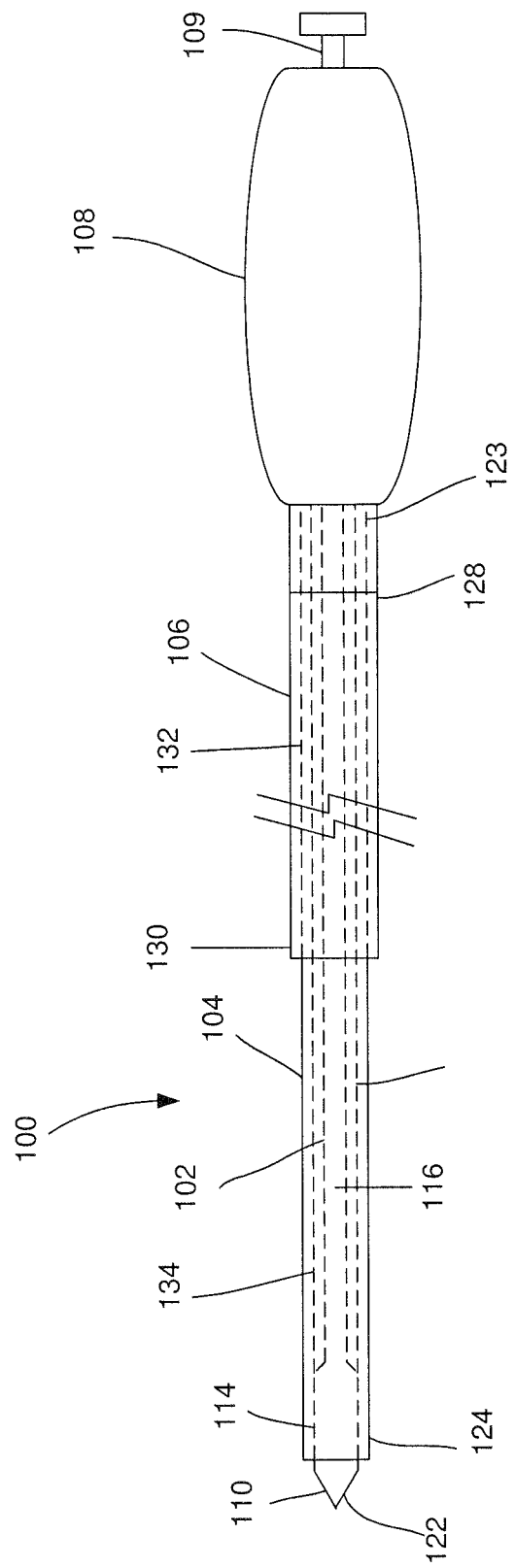
FIG. 1 shows a longitudinal cross-sectional view of a system according to an exemplary embodiment of the present disclosure.

The present disclosure may be further understood with reference to the following description and the appended drawings, wherein like elements are referred to with the same reference numerals. The present disclosure is directed to endoscopic medical devices and, in particular, relate to endoscopic ultrasound (EUS) guided drainage. Exemplary embodiments describe a EUS guided drainage systems comprising a stylet for injecting a fluid into a fluid-filled duct, an access sheath through which the stylet is inserted and a dilating sheath for dilating the fluid-filled duct to facilitate drainage. It will be understood by those of skill in the art that the system and method of the present disclosure may be used to drain, for example, a bile duct, a pancreatic duct, cysts, gallbladder, etc. It should be noted that the terms "proximal" and "distal" as used herein are intended to refer to a direction toward (proximal) and away from (distal) a user of the device.

As shown in FIGS. 1-6, a system 100 according to an exemplary embodiment of the present disclosure comprises a stylet 102 for puncturing a fluid-filled tract and injecting a fluid (e.g., contrast media) thereinto and an access sheath 104 for providing access into the fluid-filled tract. The system 100 further comprises a dilating sheath 106 for dilating the tract to facilitate drainage. The system 100 is sized and shaped to be passed through a working channel of an endoscope to be visualized under ultrasound guidance. The system 100 may further comprise a handle assembly 108, which remains outside of a living body while the stylet 102 and the access sheath 104 are inserted therein (e.g., along a body lumen accessed via a naturally occurring body orifice). The handle assembly 108 permits the stylet 102 to be removed therefrom while the access sheath 104 remains in the target duct. The handle assembly 108 also includes an actuator for advancing the dilating sheath 106 over the access sheath 104 and into the target duct.

Figure 2:
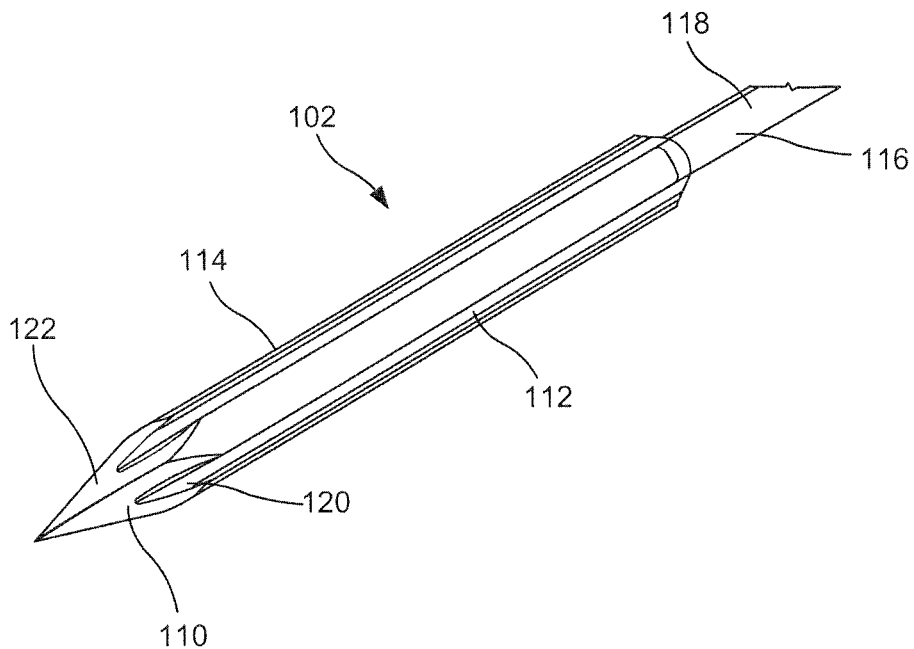
FIG. 2 shows a longitudinal cross-sectional view of a distal portion of a stylet of the assembly of FIG. 1.

As shown in FIG. 2, a stylet 102 extends along a longitudinal axis from a proximal end 109 to a distal end 110 and includes a channel 112 extending therethrough. The stylet 102 may be formed of a flexible material so that the stylet 102 may be passed along tortuous paths, for example, along a natural body lumen. In one exemplary embodiment, the stylet 102 may formed of nitinol for both flexibility and superelasticity. It will be understood by those of skill in the art, however, that the stylet 102 may be formed of any of a variety of flexible materials. The distal end 110 includes a tapered distal tip 122 for puncturing the target duct. A distal portion 114 of the stylet 102 may have a larger diameter than a proximal portion 116 of the stylet 102 extending proximally therefrom. A length of the distal portion 114 of the stylet 102 may range from between 0.3 cm and 5.0 cm, and, in particular, may be about 1 cm. A proximal portion 118 of the channel 112 extends through the proximal portion 116 of the stylet 102 along the longitudinal axis thereof while a distal portion 120 of the channel 112 extending through the distal portion 114 of the stylet 102 is defined by an annular space extending about the longitudinal axis of the stylet 102. A fluid such as, for example, a contrast media, may be injected into the target duct via the channel 112 to verify that the target duct is filled with fluid (e.g., digestive fluid).

Figure 3:
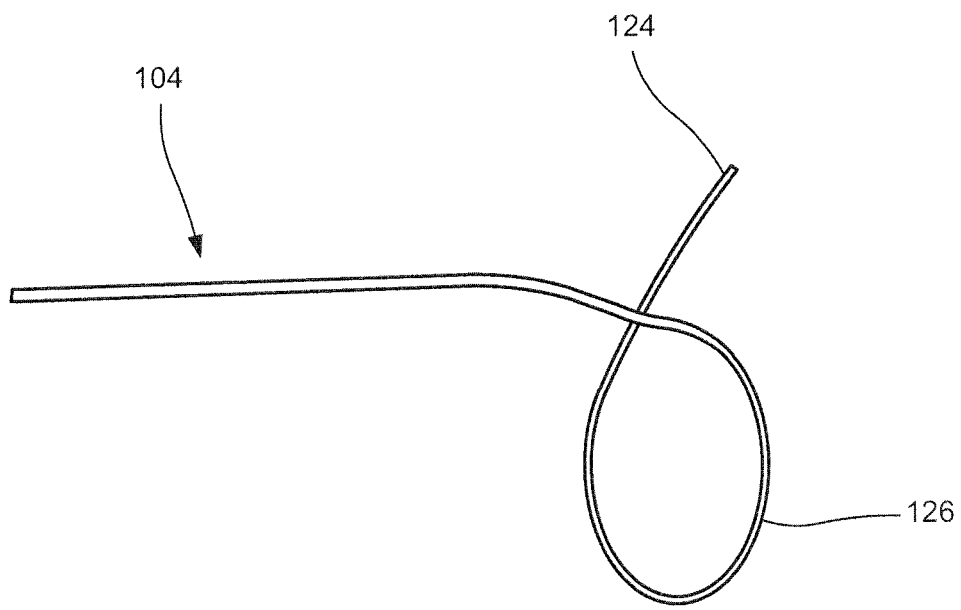
FIG. 3 shows a side view of an access sheath according to the system of FIG. 1.
Figure 4:
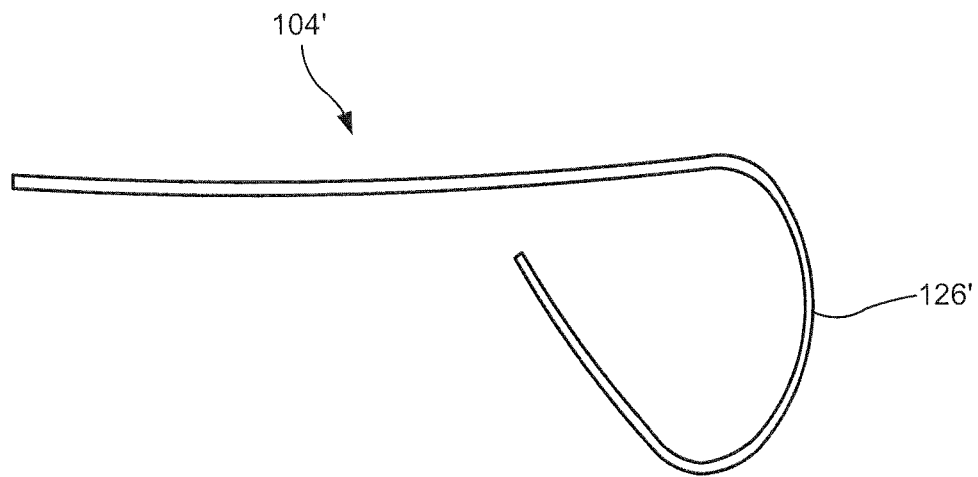
FIG. 4 shows a side view of an access sheath according to another exemplary embodiment of the present disclosure.
Figure 5:
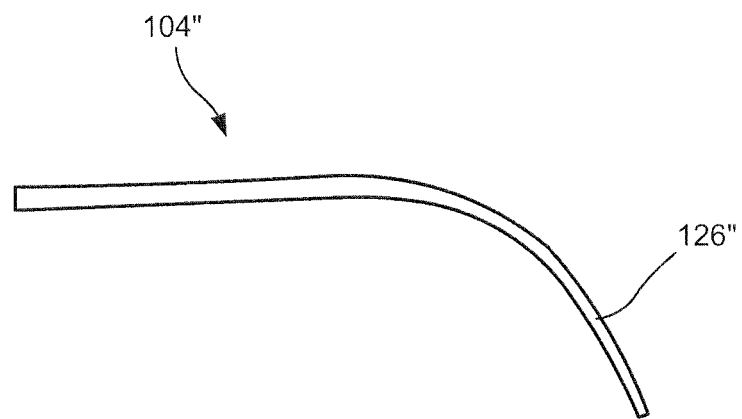
FIG. 5 shows a side view of an access sheath according to yet another exemplary embodiment of the present disclosure.

As shown in FIG. 1, the access sheath 104 extends longitudinally from a proximal end 123 to a distal end 124 and includes a lumen 134 extending therethrough. The lumen 134 is sized and shaped to slidably receive the stylet 102 therein. In particular, an inner diameter of the lumen 134 in this embodiment substantially corresponds to an outer diameter of the distal portion 114 of the stylet 102 so that when the stylet 102 is received therein, the distal portion 114 completely fills the lumen 134 of the access sheath 104 to facilitate puncturing of the target duct when the access sheath 104, with the stylet 102 received therein, is inserted into the target duct. As shown in FIG. 3, the access sheath 104 may be biased to assume a desired a curvature along a distal portion 126 thereof. In one exemplary embodiment, the distal portion 126 of the access sheath 104 is biased toward a pigtail configuration particularly suited for stabilizing the access sheath 104 in the target duct. In another exemplary embodiment, as shown in FIG. 4, a distal portion 126' of an access sheath 104' has a shepherd's crook configuration (i.e., a curve which directs the distal end of the sheath 104' back toward more proximal portions thereof) particularly suited for directing a guidewire in a desired direction within the target duct. In yet another exemplary embodiment, as shown in FIG. 5, a distal portion 126" of an access sheath 104" is biased toward a J-shaped configuration (i.e., a curve in which the distal portion 126" arcs away from an axis of more proximal portions of the sheath 104" along an arc of 90° or less) for directing a guidewire in another desired direction in the target duct.

The access sheath 104 may be formed of a polymeric material that is sufficiently flexible so that when the stylet 102 is received therein, the distal portion 126 of the access sheath 104 is straightened. Once the stylet 102 is removed therefrom, however, the distal portion 126 of the access sheath 104 is permitted to revert to its curved configuration. In an exemplary embodiment, the access sheath 104 is formed of braid reinforced polyamide. In another embodiment, the access sheath 104 is formed of multiple layers such as, for example, PTFE, braids, polyether block amide for kink resistance.

The dilating sheath 106 similarly extends longitudinally from a proximal end 128 to a distal end 130 and includes a lumen 132 extending therethrough. The lumen 132 is sized and shaped to slidably receive the access sheath 104 therein so that the dilating sheath 106 may be advanced over the access sheath 104 to the target duct to dilate the obstructed duct, thereby facilitating drainage thereof. The dilating sheath 106 may be a cold dilator such as, for example, a sohendra type dilator and/or a balloon dilator. Alternatively, the dilating sheath 106 may be a hot dilator such as, for example, a cystome or needleknife, which includes electrosurgical capabilities. For example, the dilating sheath 106 may include an electrode along the distal end 130 thereof for cauterizing tissue. In particular, the dilating sheath 106 may be configured to utilize electrosurgical dissection to facilitate dilation or to burn a lesion as the dilating sheath 106 is inserted into the target duct. In embodiments in which the dilating sheath 106 includes an electrode, the sheath 106 may include a second lumen (not shown) extending therethrough for carrying power to the electrode. The distal end 130 of the dilating sheath 106, however, may have any of a variety of configurations facilitating insertion into the target duct. In another example, the distal end 130 may be tapered. Once the dilating sheath 106 is advanced over the access sheath 104 and inserted into the target duct, the dilating sheath 106 may be actuated to dilate or expand the target duct. For example, the dilating sheath 106 may have one or more stepped diameters at discrete distances from the distal end or one or more additional sheaths that may be independently actuated to expand the path to the target duct.

Figure 6:
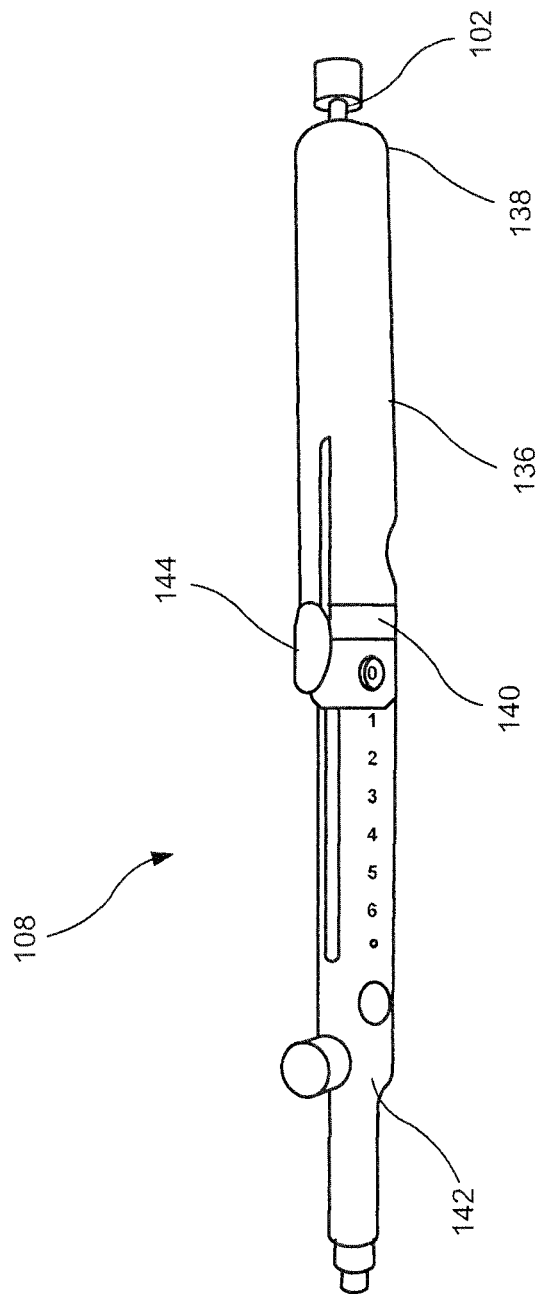
FIG. 6 shows a perspective view of a handle assembly of the system of FIG. 1.

As shown in FIG. 6, the handle assembly 108 includes a grip portion 136 extending from a proximal end 138 to a distal end 140 and an extension portion 142 coupled to the distal end 140 of the grip portion 136 and couplable to the proximal end 128 of the dilating sheath 106. The access sheath 104 may be received within and coupled to the grip portion 136 such that the access sheath 104 extends through the lumen 132 of the dilating sheath 106. The stylet 102 extends through the grip portion 136 and the extension portion 142 with the proximal end of the stylet 102 extending proximally of the proximal end 138 of the grip portion and length of the stylet 102 extending through the lumen 134 of the access sheath 104. Since the proximal end 109 of the stylet 102 extends proximally from the grip portion 136, the stylet 102 may be removed from the access sheath 104 by simply pulling the stylet 102 proximally relative to the handle assembly 108. The distal end 110 of the stylet 102 extends distally past the distal end 124 of the access sheath 104 so that the tapered tip 122 may puncture the target duct once the system 100 has been inserted into the body. The handle assembly 108 also includes an actuator 144 which moves the dilating sheath 106 longitudinally relative to the access sheath 104. In particular, the actuator 144 may include a tab that is moved distally and proximally with respect to the grip portion 136 of the handle assembly 108 to advance and retract, respectively, the dilating sheath 106 over the access sheath 104.

According to a method using the system 100 according to an exemplary embodiment of the present disclosure, the system 100 is inserted through a working channel of an endoscope via ultrasound guidance to a target duct within the body. In an insertion configuration, the access sheath 104 may be fully housed within the dilating sheath 106 to protect the endoscope through which the system 100 is inserted from the sharp distal tip 122 of the stylet 102. Upon insertion through the endoscope, the dilating sheath 106 may be retracted so that the dilating sheath 106 does not extend over the portion of the access sheath 104 being inserted into the target duct. At this point, the distal end 110 of the stylet 102 extends distally past the distal end 124 of the access sheath 104. The distal tip 122 of the stylet 102 is then advanced distally to penetrate the target duct. Once the stylet 102 and the access sheath 104 have been inserted into the target duct, a contrast media (e.g., radiopaque dye) is inserted through the channel 112 of the stylet 102 into the target duct so that a user of the system 100 may visually verify that the duct has been filled with fluid and requires drainage. The stylet 102 may then be removed from the access sheath 104 by drawing the stylet 102 proximally relative to the access sheath 104 so that only the access sheath 104 remains in the target duct. Upon removal of the stylet 102, the distal portion 126 of the access sheath 104 is freed to revert to the curved configuration to either anchor the access sheath 104 in the target duct or to direct a guidewire therethrough in a desired direction. If the access sheath 104 is not anchored in the target duct, a guidewire may be inserted through the lumen 134 of the access sheath 104 and into the target duct. A tip of the guidewire is directed in a direction corresponding to a curvature of the distal portion 126 of the access sheath 104 to contact an interior surface of the target duct to anchor the access sheath 104 thereto. The access sheath 104 may be rotated by manipulating a portion of the handle assembly 108 to direct the curved configuration in a desired direction.

Once the access sheath 104 has been anchored in the target duct, the dilating sheath 106 is advanced over the access sheath 104 into the target duct. As described above, the dilating sheath 106 is advanced by moving the actuator 144 distally with respect to the grip portion 136 of the handle assembly 108. The distal end 130 of the dilating sheath 106 is configured to facilitate insertion of the dilating sheath 106 into the target duct. In one embodiment, an electrode at the distal end 130 is activated to electrosurgically dissect and/or cauterize a surface tissue of the target duct to facilitate insertion therein. The dilating sheath 106 may be activated to dilate the target duct, enlarging the duct beyond an obstruction thereof to permit drainage of the target duct. It will be understood by those of skill in the art that the dilating sheath 106 may dilate the target duct in any of a number of ways. In one example, the dilating sheath 106 may include an expansible balloon activated to expand the target duct. It will be understood by those of skill in the art that a user may also implement further treatment of the blocked duct. In particular, a stent may be inserted into the target into the target duct, maintaining the duct in an enlarged configuration to ensure continued drainage thereof.

It will be apparent to those skilled in the art that various modifications may be made in the present disclosure, without departing from the scope of the disclosure. Thus, it is intended that the present disclosure cover the modifications and variations of his disclosure provided that they come within the scope of the appended claims and their equivalents.

What is claimed is:

1. A system for endoscopic ultrasound guided drainage, comprising:
   an access sheath extending longitudinally from a proximal end to a distal end and including an access lumen extending therethrough from the proximal end to the distal end;
   a stylet slidably received within the access lumen, the stylet extending longitudinally from a proximal end to distal end and including a channel extending therethrough, the channel configured to receive a fluid therethrough; and
   a dilating sheath extending longitudinally from a proximal end to a distal end and including a dilating lumen extending therethrough, the dilating lumen sized and shaped to slidably receive the access sheath, the dilating sheath including a stepped diameter increase at a discrete distance from the distal end.

2. The system of claim 1, wherein the access sheath includes a distal portion biased toward a curved configuration.

3. The system of claim 2, wherein the access sheath is formed of a flexible polymeric material which permits the curved distal portion to be moved to a straightened configuration when the stylet is received therein.

4. The system of claim 2, wherein the curved configuration is one of a pigtail loop, a J-shape and a shepherd's crook.

5. The system of claim 1, wherein the stylet includes a distal portion having a diameter larger than a remaining length of the stylet extending proximally from the distal portion.

6. The system of claim 1, wherein a portion of the channel extending through the distal portion of the stylet is defined by an annular space extending about a longitudinal axis of the stylet.

7. The system of claim 1, further comprising a handle assembly coupled to a proximal end of each of the stylet, access sheath and dilating sheath.

8. The system of claim 7, wherein the handle assembly includes an actuator for moving the dilating sheath longitudinally relative to the access sheath.

9. The system of claim 1, the dilating sheath including an electrode at a distal end thereof configured to cauterize tissue.

10. The system of claim 1, wherein the dilating sheath includes a plurality of stepped diameter increases at discrete distances from the distal end.

11. A system for endoscopic drainage, comprising:
    an access sheath extending longitudinally from a proximal end to a distal end and including an access lumen extending therethrough from the proximal end to the distal end;
    a stylet slidably received within the access lumen, the stylet extending longitudinally from a proximal end to distal tip and including a channel extending therethrough, the channel configured to receive a fluid therethrough, a distal portion of the stylet having a larger diameter than a remaining portion of the stylet extending proximally therefrom, the diameter of the distal portion of the stylet corresponding to a diameter of the access lumen to facilitate puncturing of a target tissue; and
    a dilating sheath extending longitudinally from a proximal end to a distal end and including a dilating lumen extending therethrough, the dilating lumen sized and shaped to slidably receive the access sheath, the dilating sheath including a stepped diameter increase at a discrete distance from the distal end.

12. The system of claim 11, wherein the access sheath includes a distal portion biased toward a curved configuration.

13. The system of claim 11, further comprising a handle assembly coupled to a proximal end of each of the stylet, access sheath and dilating sheath.

14. The system of claim 11, wherein a portion of the channel extending through the distal portion of the stylet is defined by an annular space extending about a longitudinal axis of the stylet.

15. The system of claim 13, wherein the access sheath is formed of a flexible polymeric material which permits the curved distal portion to be moved to a straightened configuration when the stylet is received therein.

16. The system of claim 13, wherein the handle assembly includes an actuator for moving the dilating sheath longitudinally relative to the access sheath.

17. A method for endoscopic ultrasound guided drainage, comprising:

inserting an access sheath and a stylet through a working channel of an endoscope into a target duct within a body, the stylet extending through a lumen of the access sheath such that a distal tip of the stylet extends distally past a distal end of the access sheath so that the distal tip punctures the target duct;

injecting a contrast media through a channel of the stylet into the target duct to visually verify that the target duct is filled with fluids; and advancing a dilating sheath distally over the access sheath and into the target duct to dilate the target duct.

18. The method of claim 17, wherein the target duct is one of a bile duct, pancreatic duct, a cyst and a gallbladder.

19. The method of claim 17, further comprising removing the stylet from the access sheath so that a distal portion of the access sheath reverts to a curved configuration.

20. The method of claim 17, further comprising cauterizing a surface of the target duct via an electrode of the dilating sheath.

21. The method of claim 17, further comprising inserting a stent into the target duct to maintain the target duct in an enlarged configuration to ensure continued drainage thereof.

* * * * *